United States Patent
Schlegel

(10) Patent No.: US 11,160,743 B2
(45) Date of Patent: Nov. 2, 2021

(54) PREPARATION OF NANO-SIZED UV ABSORBERS

(71) Applicant: DSM IP ASSETS B.V., Heerlen (NL)

(72) Inventor: Bernd Schlegel, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/339,501

(22) PCT Filed: Oct. 9, 2017

(86) PCT No.: PCT/EP2017/075584
§ 371 (c)(1),
(2) Date: Apr. 4, 2019

(87) PCT Pub. No.: WO2018/069200
PCT Pub. Date: Apr. 19, 2018

(65) Prior Publication Data
US 2019/0282483 A1    Sep. 19, 2019

(30) Foreign Application Priority Data
Oct. 11, 2016  (EP) .................................... 16193205

(51) Int. Cl.
| | | |
|---|---|---|
| A61K 8/49 | (2006.01) | |
| A61K 8/04 | (2006.01) | |
| A61K 8/60 | (2006.01) | |
| A61Q 17/04 | (2006.01) | |
| A61K 8/02 | (2006.01) | |

(52) U.S. Cl.
CPC .......... *A61K 8/4966* (2013.01); *A61K 8/0241* (2013.01); *A61K 8/04* (2013.01); *A61K 8/602* (2013.01); *A61K 8/604* (2013.01); *A61Q 17/04* (2013.01); *A61K 2800/413* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 5,145,684 A | 9/1992 | Liversidge et al. | |
| 6,521,217 B1 * | 2/2003 | Luther | A61K 8/496 424/59 |
| 8,393,556 B2 | 3/2013 | Müller et al. | |

FOREIGN PATENT DOCUMENTS

| | | | | |
|---|---|---|---|---|
| CN | 101687823 | | 3/2010 | |
| EP | 0 499 299 | | 8/1992 | |
| JP | 4-295420 | | 10/1992 | |
| JP | 2010-531842 | | 9/2010 | |
| WO | 2009/003934 | | 1/2009 | |
| WO | WO 2009/003934 | * | 1/2009 | ........... C07D 251/24 |
| WO | WO2009/003934 | * | 2/2009 | ........... C07D 251/24 |
| WO | 2009/063392 | | 5/2009 | |

OTHER PUBLICATIONS

Herzog et al (J Colloid and Interface Sci 271:163-144, 2004) (Year: 2004).*
International Search Report for PCT/EP2017/075584 dated Nov. 21, 2017, 3 pages.
Written Opinion of the ISA for PCT/EP2017/075584 dated Nov. 21, 2017, 7 pages.

* cited by examiner

*Primary Examiner* — Craig D Ricci
(74) *Attorney, Agent, or Firm* — Nixon & Vanderhye P.C.

(57) ABSTRACT

The invention relates to an improved process for the manufacture of nano-sized organic UV absorbers having a mean particle size distribution ($D_v 50$) determined by light scattering of less than 200 nm.

11 Claims, No Drawings

PREPARATION OF NANO-SIZED UV ABSORBERS

The invention relates to an improved process for the manufacture of nano-sized organic UV absorbers having a mean particle size distribution ($D_v50$) determined by light scattering of less than 200 nm.

Nano-sized organic UV-absorbers such as for example Methylene Bis-Benzotriazolyl Tetramethylbutylphenol (Tinosorb® M) are highly effective UV-absorbers which may, for example, be used as light screening agents in cosmetic products.

The particle size of micronized organic UV absorbers is a critical parameter for their effectiveness. Micronized organic UV-light absorbing compounds having a particle size in the nano-size range have been shown to be effective UV-absorbers for the protection of skin against the harmful effect of UV radiation. With conventional grinding technologies using SAZ ceramic grinding beads, however, such micronized organic UV-filter compounds can only be obtained with a high energy input.

WO2009003934 discloses a process for the preparation of insoluble organic UV absorbers in the nano-size range which overcomes the drawback of the prior art as it requires only a moderate energy input. Said process encompasses milling the organic UV absorbers in a ball mill comprising yttrium stabilized zirconium oxide grinding beads in the presence of an alkyl polyglucoside which is Plantacare 200 UP, a $C_8$ to $C_{16}$ alkyl poly-glucosides (also referred to under the ambiguous INCI name 'decyl glucoside') and an antifoam agent as dispersing agent auxiliary.

The drawback of the process disclosed in WO 2009003934 is, however, that an antifoam agent is necessary to control foaming during the ball milling process. There is however, a need of a product form, which does not include an antifoaming agent as this is not desirable for all end-product applications.

Thus, there is an ongoing need in the art to develop a simple, industrially feasible and scalable process for the preparation of micronized insoluble organic UV-absorbers by ball milling which is carried out in the absence of an antifoam agent while requiring a low energy input.

Surprisingly it has been found that the foaming can be significantly reduced if the coarse particles of the insoluble organic UV absorber (in the form of its dry powder) used in the suspensions subjected to the ball-milling exhibit a standardized particle size distribution Dv90 determined by laser diffraction of less than 150 μm. Another advantage is that suspensions comprising such coarse particles of the insoluble organic UV-filter are more liquid and can thus more easily be degassed and dosed. It has furthermore been found that the use of a specific alkyl polyglucoside further reduces the foaming.

Thus, the present invention relates to a process (A) for the preparation of an aqueous dispersion of a nano-sized insoluble organic UV absorber having a particle size Dv50 determined by light scattering of less than 200 nm, said process comprising the step of milling a suspension of coarse particles of the insoluble organic UV absorber in a mixture of water and an alkyl polyglucoside in a ball mill using yttrium-stabilized zirconium oxide grinding beads until the particle size Dv50 of less than 200 nm is obtained, characterized in that the coarse particles of the insoluble organic UV absorber exhibit a particle size Dv90 determined by laser diffraction in the range of 1 to 200 μm.

All particle sizes of the nano-sized insoluble organic UV absorber obtained in the ball-milling step are determined by light scattering (i.e. Photon Correlation Spectroscopy (PCS)) using a Beckman Coulter Delsa Nano S. Further information on this particle size characterization method can e.g. be found in 'Particle Characterization: Light Scattering Methods' by Renliang Xu, Kluwer Academic Publishers (ISBN 0-306-47124-8). If nothing else is stated all particle sizes referring to the nano-sized insoluble organic UV absorber are Dv50 values (volume diameter, 50% of the population resides below this point, and 50% resides above this point) determined by light scattering. The particle size is generally determined in a suspension of the nano-sized insoluble organic UV absorber in water such as ultrapure water (Mili-Q purified), preferably at a concentration level of 3 mg/ml.

Preferably, in all embodiments of the present invention, the particle size Dv50 of the nano-sized insoluble organic UV absorber obtained in the ball milling step is in the range of 50 to 150 nm, more preferably in the range of 75 to 125 nm, most preferably in the range of 80 to 110 nm. In an even more preferred embodiment the nano-sized insoluble organic UV absorber exhibits a Dv10 in the range of 50 to 80 nm, a Dv50 in the range of 75 to 125 nm and a Dv90 in the range of 140 to 180 nm, more preferably Dv10 in the range of 55 to 75 nm, a Dv50 in the range of 80 to 110 nm and a Dv90 in the range of 150 to 175 nm All particle sizes of the coarse particles of the insoluble organic UV absorber to be used in the ball milling step are determined by laser diffraction technique using a "Mastersizer 3000" of Malvern Instruments Ltd., UK. Further information on this particle size characterization method can e.g. be found in "Basic principles of particle size analytics", Dr. Alan Rawle, Malvern Instruments Limited, Enigma Business Part, Grovewood Road, Malvern, Worcestershire, WR14 1XZ, UK and the "Manual of Malvern particle size analyzer". Particular reference is made to the user manual number MAN 0096, Issue 1.0, November 1994. If nothing else is stated all particle sizes referring to the coarse particles of the insoluble organic UV absorber are Dv90 values (volume diameter, 90% of the population resides below this point, and 10% resides above this point) determined by laser diffraction. The particle size can be determined in the dry form, i.e. as powder or in suspension. Preferably, the particle size of the coarse particles of the insoluble organic UV-filter is determined as powder.

Preferably, in all embodiments of the present invention, the coarse particles of the insoluble organic UV absorber exhibit a Dv90 determined by laser diffraction in the range of 1 to 150 μm, preferably in the range of 25 to 125 μm, most preferably in the range of 50 to 100 μm, such as in particular in the range of 75-90 μm. In a particular preferred embodiment, the coarse particles of the insoluble organic UV absorber exhibit a Dv10 in the range of 1 to 15 μm, a Dv50 in the range of 10 to 40 μm and a Dv90 in the range of 70 to 100 μm, more preferably a Dv10 in the range of 5 to 10 μm, a Dv50 in the range of 20 to 35 μm and a Dv90 in the range of 75 to 90 μm.

The term 'insoluble' refers to an UV absorber which exhibits a solubility in common cosmetic oils such as e.g. $C_{12-15}$ alkyl benzoate, propyleneglycol, mineral oil but also in water of less than 0.01 wt.-%, preferably of less than 0.05 wt.-%, most preferably of less than 0.03 wt.-%.

Preferably, the UV absorber is selected from the compounds of formula (I)

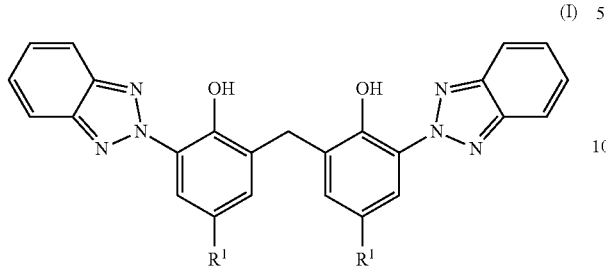

wherein $R^1$ is a $C_1$-$C_{18}$alkyl group, which is optionally substituted by phenyl.

Examples of $C_1$-$C_{18}$alkyl groups are branched or unbranched alkyl groups such as methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,3,3-tetramethylbutyl group 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, and n-dodecyl. Preferably $R^1$ is a branched $C_3$-$C_8$alkyl group such as most preferably a 1,1,3,3-tetramethylbutyl group.

Most preferred a in all embodiments of the present invention the UV absorbers of formula (I) is a compound of formula (Ia)

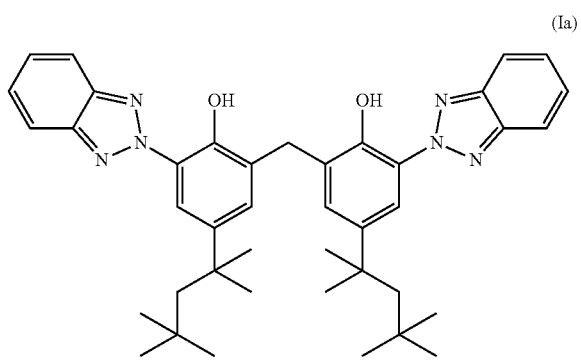

which is known as 2,2'-methylene-bis-(6(2H-benzotriazol-2-yl)-4-(1,1,3,3-tetramethylbutyl)-phenol [CAS 103597-45-1].

The coarse particles of the insoluble organic UV absorber can for example be prepared by appropriate crystallization or dry or wet pre-milling e.g. with a colloidal mill. Suitable coarse particles of 2,2'-methylene-bis-(6(2H-benzotriazol-2-yl)-4-(1,1,3,3-tetramethylbutyl)-phenol can e.g. be obtained by buying Grandsorb UV 360 as supplied by Hongkun Group, China and selection of batches exhibiting an appropriate particle size Dv90.

In a particular embodiment, the invention relates to a process (B) for the preparation of an aqueous dispersion comprising a nano-sized insoluble organic UV absorber, which is a process (A) with all the preferences and definitions as outlined above comprising the consecutive steps of
(i) suspending the coarse particles of the insoluble organic UV absorber in a mixture of water and an alkyl polyglucoside followed by
(ii) milling the thus obtained suspension in a ball mill comprising yttrium-stabilized zirconium oxide grinding beads until a particle size Dv50 determined by light scattering of less than 200 nm is obtained.

In a particular embodiment, the process (B) encompasses an additional step (ia), which takes place after step (i) which step is a degassing of the obtained suspension (i.e. removing gas bubbles suspended therein) e.g. by stirring. Preferably, the degassing takes place over a time of 0.5 to 3 hours, more preferably over a time of 1 to 2 hours and at a temperature selected in the range of 20 to 80° C., preferably in the range of 50 to 80° C., most preferably in the range of 55 to 75° C., such as in the range of 60 to 70° C. Most preferably, the degassing takes place for a period of about 1 to 2 hours at a temperature selected in the range of 60-70° C., and is followed by cooling down the suspension, most preferably to RT (i.e. about 20-22° C.).

The alkyl polyglucoside preferably exhibits the formula $$C_nH_{2n+1}O(C_6H_{10}O_5)xH \qquad (II)$$

wherein n is and integer from 8 to 16, and
x is the mean polymerisation level of the glucoside moiety ($C_6H_{10}O_5$) and ranges from 1 to 1.7, preferably from 1.1 to 1.7, such as from 1.2 to 1.7, respectively from 1.4 to 1.6.

Suitable alkyl polyglucoside according to the present invention are the alkyl polyglucosides known under the INCI name 'decyl glucoside' [CAS 68515-73-1], such as in particular the $C_{8-16}$ alkyl polyglucoside which is e.g. available as PlantaCare 2000 UP from BASF or the $C_{8-10}$ alkyl polyglucoside which is e.g. commercially available as APG Green APG 0810 from Zhejiang Taizhou Tu-Poly Co. Ltd or Glucopon 225DK from Cognis.

Particularly advantageous alkyl polyglucosides according to the present invention are $C_{8-10}$ alkyl polyglucoside, more preferably the ones consisting essentially of caprylyl ($C_8$) and capryl ($C_{10}$) polyglucosides. Preferably such caprylyl ($C_8$) and capryl ($C_{10}$) polyglucosides furthermore exhibit a ratio (%/%, wherein all % are area-% determined by HPLC-MS) of caprylyl ($C_8$) monoglucoside to capryl ($C_{10}$) monoglucoside in the range of 3:1 to 1:3, preferably in the range of about 2:1 to 1:2, most preferably in the range of 1.5:1 to 1:1.5. Additionally, such $C_{8-10}$ alkyl polyglucoside preferably contain no more than 3 wt.-%, more preferably no more than 2 wt.-%, most preferably no more than 1.5 wt.-% of $C_{12}$ alkyl monoglucoside as determined by HPLC-MS and illustrated in the example. It is understood, that such alkyl polyglucosides are free of any (i.e. contain no) higher (i.e. $C_{14-16}$) alkyl polyglucosides.

These $C_{8-10}$ alkyl polyglucosides furthermore preferably exhibit a mean polymerisation level of the glucoside moiety x ranging from 1 to 1.7, preferably from 1.1 to 1.6, most preferably from 1.1 to 1.4 such as in particular in the range of 1.1 to 1.3.

Furthermore, the $C_{8-10}$ alkyl polyglucoside according to the invention consisting essentially of caprylyl ($C_8$) and capryl ($C_{10}$) polyglucosides contains advantageously at least 60%, preferably at least 65%, most preferably at least 70% of the respective mono-glucosides as e.g. determined by HPLC-MS.

It is furthermore preferred that the $C_{8-10}$ alkyl polyglucoside according to the present invention are substantially (i.e.

essentially) free of any $C_9$ alkyl polyglucosides, i.e. contain essentially no $C_9$ alkyl polyglucosides. This means that the amount of any $C_9$ alkyl polyglucosides in the $C_{8-10}$ alkyl polyglucoside is less than 0.1 wt.-%, preferably less than 0.05 wt.-%, most preferably less than 0.01% such as in particular less than 0.005 wt.-%, based on the total weight of the $C_{8-10}$ alkyl polyglucoside.

Most preferred in all embodiments according to the present invention is the use of $C_{8-10}$ alkyl polyglucoside such as the $C_{8-10}$ alkyl polyglucoside made from glucose derived from corn and $C_8$ and $C_{10}$ fatty alcohols derived from coconut and palm kernel oils, which is e.g. sold as an aqueous dispersion under the tradename Green APG 0810 by Shanghai Fine Chemical as this leads to a further reduction of the foaming compared to the use of the $C_{8-16}$ alkyl polyglucoside.

The water used in the process according to the present invention is preferably purified water such as in particular de-ionized (DI) water wherein most of the mineral content and dissolved ion content, such as the ions, calcium, sodium, and chlorides have been removed. DI water is classified into several types dependent on its use. Preferably type II DI water or type III DI water (according to U.S. National Committee for Clinical Laboratory Standards (NCCLS): Maximum Contaminant Levels in Type I-III Purified Water) is used in the process according to the present invention.

The suspension prepared in step (i) consists preferably of
a) 45-55 wt.-% of the coarse particles of the insoluble organic UV absorber, preferably 48-52 wt.-%,
b) 10-20 wt.-% of the alkyl polyglucoside, preferably 13-17 wt.-%, and
c) 25-40 wt.-% of water, preferably 30-35 wt.-%,
based on the total weight of the suspension and with the proviso that the sum of the ingredients a) to c) sum up to 100 wt.-%.

The term 'consisting of' as used according to the present invention means that the total amount of the insoluble organic UV absorber, the alkyl polyglucoside and the water ideally sums up to 100 wt.-%. It is however not excluded that small amount of impurities or additives may be present which are introduced via the respective raw materials. It is, however, well understood that the suspensions used in the ball milling process according to the present invention contain no antifoam agent.

The temperature in the ball milling step is not critical and can easily be chosen by a person in the art. Preferably the ball milling is performed at a temperature selected in the range of 20 to 45° C., such as preferably in the range of 25-35° C. (measured in the suspension vessel).

The yttrium-stabilized zirconium oxide grinding beads used in the present invention exhibit a high density and are highly spherical which makes them particularly suitable for horizontal mills. Typical yttrium-stabilized zirconium oxide grinding beads according to the present invention have the following properties:
Chemical Composition: 95% $ZrO_2$, 5% $Y_2O_3$
Specific Density: 6.1 g/cm³
Bending Strength: 1200 MPa
Hardness (Hv10): 1250
Modulus of Elasticity: 210 GPa
15 Fracture Toughness: 6.0 Mpam⁰
Such grinding beads are e.g. commercially available at Tosho Ceramics, Japan.

The diameter of the grinding beads is preferably selected in the range of 0.1-0.5 mm, preferably in the range of 0.1 to 0.4 mm, more preferably in the range of 0.2 to 0.4 mm, most preferably in the range of 0.25 to 0.35 mm as this results in particular good results in view of foaming and final particle size distribution of the nano-sized insoluble organic UV absorber.

As ball milling apparatus for the preparation of the insoluble, nano-sized organic UV absorbers there may be used, for example, modern ball mills; manufacturers of these types of mill are, for example, Netzsch (LMZ mill), or Bachhofer. Preferred milling apparatus according to the present invention are agitated ball mills such as LMZ's by Netzsch (e.g. LMZ 4 or LMZ 60) as well as Dyno-Mill ECM-AP from Willy A. Bachofen A G.

Thus, the present invention also encompasses the processes according to the invention, wherein the ball mill is selected from the group consisting of a LMZ and Dyno-Mill ECM-AP.

In order to avoid settlement of the nano-sized UV absorber in the aqueous dispersion obtained in the milling (step (ii)), preferably a suitable thickener such as xanthan gum [CAS 11138-66-2], gellan gum [CAS 71010-52-1] and/or carboxymethylcellulose [CAS 9000-11-7/9004-32-4], preferably xanthan gum is added in a subsequent step, preferably after removal of the grinding beads. A particular preferred xanthan gum grade to be used according to the present invention is available as Rhodicare S which has a viscosity of 1200-1600 cps as 1% solution in KCl (Brookfield LVT, 60 rpm, spindle 3, 24° C.).

The amount of thickener added to the aqueous dispersion comprising the nano-sized insoluble organic UV absorber according to the invention is preferably selected in the range of 0.05 to 2 wt.-%, such as more preferably in the range of 0.1 to 1 wt.-%, such as most preferably in the range of 0.1 to 0.5 wt.-%, based on the total weight of the aqueous dispersion.

Preferably the viscosity of the aqueous dispersion comprising the nano-sized insoluble organic UV absorber according to the invention is selected in the range of 50 to 1500 mPas such as preferably in the range of 100 to 1250 mPas, and most preferably of 100 to 1000 mPas (according to DIN 53019).

In addition, the aqueous dispersion comprising the nano-sized insoluble organic UV absorber according to the invention advantageously further comprises an additional amount of propylene glycol which is also added after the milling step (ii) and removal of the grinding beads. Preferably the amount of propylene glycol in the aqueous dispersion is selected in the range of 0.05 to 2 wt.-% such as more preferably in the range of 0.1 to 1 wt.-% such as most preferably in the range of 0.1 to 0.5 wt.-%, based on the total weight of the aqueous dispersion comprising the nano-sized insoluble organic UV absorber.

Most preferably a mixture of xanthan gum and propylene glycol is added to the aqueous dispersion after the milling step (ii) and removal of the grinding beads.

Thus, in a particular advantageous embodiment the invention encompasses a process (C), which is a process (B) with all the preferences and definitions as outlined above comprising the subsequent steps of
(iii) removal of the grinding beads followed by
(iv) addition of a mixture of a thickener, preferably xanthan gum and propylene glycol to the milled suspension.

In all embodiments of the invention the weight-ratio (w/w) of the mixture of propylene glycol and xanthan gum added to the aqueous dispersion of the nano-sized insoluble organic UV absorber is preferably selected in the range of 3:1 to 1:3, more preferably in the range of 2.5:1 to 1:1, and most preferably in the range of about 2:1.

The temperature in step (iv) is preferably selected in the range of 30 to 50° C., such as more preferably in the range of 35-45° C.

The following examples are provided to further illustrate the compositions and effects of the present invention. These examples are illustrative only and are not intended to limit the scope of the invention in any way.

EXAMPLE 1

Milling a) 22 kg of purified water was added into a 100 l vessel at 30-35° C. Afterwards 9.8 kg Green APG 0810 were added. Then 33 kg Grandsorb UV360 having a coarse particle size Dv90 of 86 µm (measured by laser diffraction with a Malvern Mastersizer 3000, powder measurement, air pressure 0.2 bar) was slowly added over a time period of 30 minutes followed by degassing the resulting suspension for 2 h under gentle stirring at 65° C. The resulting suspension was then cooled down to 25-30° C. Afterwards 50 kg of the resulting suspension was milled in a LMZ 4 using yttrium-stabilized zirconium oxide grinding beads (0.3 mm, 95% $ZrO_2$, 5% $Y_2O_3$ from Tosoh Ceramic, Japan) until a particle size Dv50 of about 100 nm (measured by light scattering with a Coulter Delsa Nano S, at an adjusted concentration of 3 mg/ml) was obtained. Only little foam formation during the milling was observed, which was well tolerated by the milling process. After removal of the grinding beads, a suspension consisting of 161 g of propyleneglycol and 80.5 g of xanthan was slowly added under gentle stirring at about 40° C. resulting in the final product form.

b) The same experiment as outlined in a) was repeated with Grandsorb UV360 having a coarse particle size Dv90 of 262 µm. In this case uncontrolled foaming shortly after the start of the milling was observed which led to the termination of the milling process.

c) The same experiment as outlined in a) was repeated with PlantaCare 2000 UP. In this case more foaming compared to Green APG 0810 during milling was observed, which was however still tolerable to run the process to the end.

EXAMPLE 2

Analytics of Alkyl Polyglucosides

The respective samples have been dissolved in a mixture of tetrahydrofurane/water (50/50), approx. 1 mg/ml, and were analysed by HPLC mass spectrometry using a reversed-phase YMC Pro $C_4$ column with a water/acetonitrile gradient with 0.1% methanesulfonic acid (5→90% acetonitrile over 15 min). Detection was performed on an Agilent 6130 single MSD operating in ES positive mode. TIC and EIC were used to determine the relative distribution of the compounds of interest. The relative distribution of the alkyl monoglucosides is outlined in table 1. All % are area-%.

TABLE 1

Relative distribution of the alkyl mono glucosides

| Sample | Relative amount [%] | |
|---|---|---|
| | Alkyl (8-16) Glucoside* | C8-C10 polyglucoside° |
| $C_8$ monoglucoside | 20.8 | 44.1 |
| $C_{10}$ monoglucoside | 16.6 | 54.7 |
| $C_{12}$ monoglucoside | 41.5 | 1.2 |
| $C_{14}$ monoglucoside | 20.1 | n.d. |
| $C_{16}$ monoglucoside | 0.9 | n.d. |

*Commercially available as Plantacare UP 2000 at Cognis; approx. absolute amount as determined by HPLC-MS of $C_8/C_{10}/C_{12}/C_{14}/C_{16}$ alkyl monoglucoside~77% (area %)
°Commercially available as Green APG 0810 at Shanghai Fine Chemicals; approx. absolute amount as determined by HPLC-MS of $C_8/C_{10}$ alkyl monoglucoside~78% (area %)
n.d.: not detected

The invention claimed is:

1. A process for the preparation of a milled suspension comprised of an aqueous dispersion of a nano-sized insoluble organic UV absorber having a particle size Dv50 determined by light scattering of less than 200 nm, wherein the process comprises the steps of:

(a) providing a suspension of coarse particles of an insoluble organic UV absorber having a particle size Dv90 determined by laser diffraction in the range of 75 to 90 µm in a mixture of water and a $C_8$-$C_{10}$ alkyl polyglucoside; and (b) milling the suspension in the absence of an anti-foam agent in a ball mill using yttrium-stabilized zirconium oxide grinding beads until the insoluble organic UV absorber has a particle size Dv50 of less than 200 nm to thereby obtain the milled suspension, wherein the insoluble organic UV absorber is a compound of formula (I):

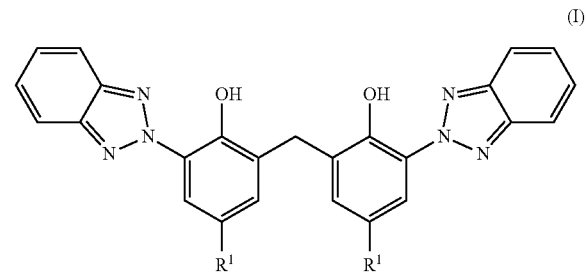

wherein $R^1$ is a $C_1$-$C_{18}$ alkyl group which is optionally substituted by phenyl.

2. The process according to claim 1, wherein step (b) is practiced until the particle size Dv50 of the nano-sized insoluble organic UV absorber is 50 to 150 nm.

3. The process according to claim 1, wherein the compound of formula (I) is a compound of formula (Ia):

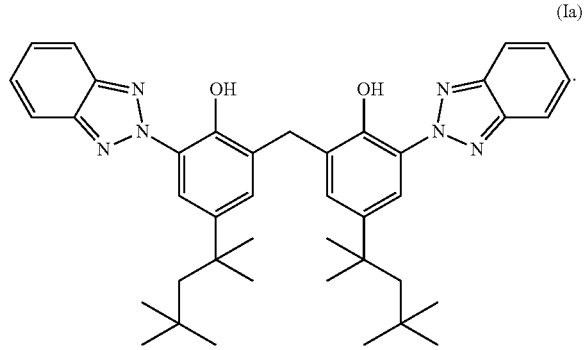 [SMILES: CC(C)(C)CC(C)(C)c1cc(Cc2cc(C(C)(C)CC(C)(C)C)cc(-n3nc4ccccc4n3)c2O)c(O)c(-n2nc3ccccc3n2)c1]
(Ia)

4. The process according to claim 1, wherein step (a) comprises a step of:
(i) suspending the coarse particles of the insoluble organic UV absorber in a mixture of water and the $C_8$-$C_{10}$ alkyl polyglucoside to obtain the suspension.

5. The process according to claim 4, wherein step (i) comprises an additional step (ia) prior to step (b), wherein step (ia) includes degassing the suspension.

6. The process according to claim 4, wherein the process further comprises the subsequent steps of:
(c) removing the grinding beads from the milled suspension, followed by
(d) adding a mixture of a thickener and propylene glycol to the milled suspension.

7. The process according to claim 6, wherein the thickener is selected from the group consisting of xanthan gum, gellan gum and carboxymethylcellulose.

8. The process according to claim 7, wherein the propylene glycol and xanthan gum are present in a weight-ratio (w/w) of the propylene glycol to the xanthan gum of 3:1 to 1:3.

9. The process according to claim 1, wherein the suspension consists of:
a) 45-55 wt.-%, based on the total weight of the suspension, of the coarse particles of the insoluble organic UV absorber,
b) 10-20 wt.-%, based on the total weight of the suspension, of the $C_8$-$C_{10}$ alkyl polyglucoside, and
c) 25-40 wt.-% of water, based on the total weight of the suspension, wherein
the ingredients a) to c) sum to 100 wt.-%.

10. The process according to claim 9, wherein the suspension consists of:
a) 48-52 wt.-%, based on the total weight of the suspension, of the coarse particles of the insoluble organic UV absorber,
b) 13-17 wt.-%, based on the total weight of the suspension, of the $C_8$-$C_{10}$ alkyl polyglucoside, and
c) 30-35 wt.-%, based on the total weight of the suspension, of water.

11. The process according to claim 1, wherein grinding beads have a diameter of 0.1-0.5 mm.

* * * * *